United States Patent
Carlsson et al.

[11] Patent Number: 5,688,528
[45] Date of Patent: Nov. 18, 1997

[54] OIL-IN WATER EMULSIONS

[75] Inventors: Anders Carlsson, Stockholm; Marina Delogu, Saltsjö-Boo; Bengt Herslöf, Stockholm, all of Sweden

[73] Assignee: Scotia LipidTeknik AB, Stockholm, Sweden

[21] Appl. No.: 676,138
[22] PCT Filed: Feb. 6, 1995
[86] PCT No.: PCT/SE95/00115
§ 371 Date: Jul. 15, 1996
§ 102(e) Date: Jul. 15, 1996
[87] PCT Pub. No.: WO95/20943
PCT Pub. Date: Aug. 10, 1995

[30] Foreign Application Priority Data

Feb. 4, 1994 [SE] Sweden .................. 9400368
Jul. 12, 1994 [SE] Sweden .................. 9402454

[51] Int. Cl.$^6$ ................................ A61K 9/127
[52] U.S. Cl. ................... 424/450; 424/45; 424/84; 424/498; 424/501; 428/402.2; 436/829; 514/963; 514/965; 514/966; 514/974
[58] Field of Search .................. 424/450, 45, 84, 424/498, 501; 428/402.2; 436/829; 514/963, 965, 966, 974

[56] References Cited

U.S. PATENT DOCUMENTS 4,610,868  9/1986  Fountain et al. .................. 424/1.1
5,151,272  9/1992  Engstrom et al. .................. 424/450

FOREIGN PATENT DOCUMENTS 0 215 313  3/1987  European Pat. Off. .
0249561  12/1987  European Pat. Off. .
WO 94/24984  11/1994  WIPO .

Primary Examiner—Terressa Mosley
Attorney, Agent, or Firm—Hoffmann & Baron, LLP

[57] ABSTRACT

The invention relates to an oil-in-water emulsion comprising 0.01–50% by weight of the total preparation, preferably 0.1–10%, of a galactolipid material as an emulsifier. The galactolipid material consists of at least 50% digalactosyldiacylglycerols, the remainder being other polar lipids. The said emulsion is suitable as a carrier for one or more active substances in a pharmaceutical composition, but also in nutritional, cosmetical, food and agricultural products.

16 Claims, No Drawings

OIL-IN WATER EMULSIONS

TECHNICAL FIELD

This invention relates to oil-in-water type emulsions comprising a polar lipid material as an emulsifier. These emulsions are suitable for use as carriers for an active substance in a pharmaceutical composition, but also in nutritional, cosmetical, food and agricultural products.

1. Background of the Invention

Emulsions of the type oil-in-water for pharmaceutical applications, such as clinical nutrition and for the administration of lipophilic drugs, are generally based on natural lipids. The oil is typically a vegetable oil such as soybean oil, safflower oil or medium-chain triacylglycerol (MCT) oil. The emulsifier is typically a phospholipid such as egg yolk phospholipids (egg lecithin) or soybean phospholipids (soy lecithin). These emulsifiers consist of mixtures of phospholipid classes, such as phosphatidylcholine and phosphatidylethanolamine, which are zwitter-ionic, and phosphatidylinositol, which is anionic. It is widely common knowledge that these lecithin emulsifiers are the most utilised natural lipids in preparing emulsions on an industrial scale of the kind mentioned above. It is also well-known that such emulsions suffer from disadvantages and problems which relate to the emulsifier being phospholipids. Such disadvantages and problems are, for example, broad particle size distributions and particle fusions resulting in so-called creaming.

Most commercial fat emulsions are based on egg phospholipids, which are produced from animal sources, in most cases egg yolk powder. Animal sources are, in some cases, related to problems connected to virus contamination, and, in the specific case of egg yolk powder, bacteria such as Salmonella. Another important feature of egg phospholipids is the content of polyunsaturated fatty esters, such as arachidonate and docosahexaenoate, which are extremely susceptible to oxidation in the presence of even small amounts of oxygen. Thus, the odour and taste of egg phospholipids are often very unpleasant, which can be carried through to the fat emulsions. Contamination and oxidation may often cause problems which relate to industrial safety and handling aspects.

2. Prior Art

EP-A2-0 402 090 discloses an edible oil-in-water emulsion suitable for creams and dressings comprising 10–99% of the entire oil and fat content of a diglyceride mixture. In order to improve the stability the emulsion can also include 0.1–10%, based on the oil phase, of phospholipids.

EP-A2-0 391 369 discloses a stable pharmaceutical composition of an oil-in-water emulsion type which comprises an effective amount of a lipophilic drug. The emulsion is composed of 3–50% of an oily carrier, mainly MCT oil, 0.05–20% of a phospholipid, 0.03–10% of a non-ionic surfactant, and 0.05–50% of an ionic surfactant. The improved stability is said to be caused by a synergism between the stated ingredients.

Glycosylglycerides are a type of glycolipids which are well-known constituents of plant cell membranes. Two types based on galactose are very common, monogalactosyldiacylglycerol, MGDG, and digalactosyldiacylglycerol, DGDG, representing up to 40% of the dry weight of the thylakoid membranes.

Plant glycolipids have carbohydrate units, mainly of galactose, linked to glycerol. In MGDG the 1-position of the galacrose ring has a β-link to glycerol, and in DGDG there is an α,1-6 bond between the sugars. A minor constituent is the plant sulpholipid, more correctly named sulphoquinovosyldiacylglycerol, SQDG, which contains a sulphonate rather than a hydroxyl group linked to carbon 6 of the terminal deoxyglucose residue. Most plant glycolipids can be described by the general formula

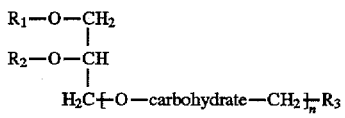

wherein $R_1$ and $R_2$ independently of each other are saturated or unsaturated fatty acid residues of 2–24 carbon atoms and 0–6 double bonds, further esterified hydroxy acids, that is estolides, or hydrogen; the carbohydrate is a monosaccharide unit; n=1–5; and $R_3$ is a hydroxyl or sulphonate group.

In investigating the interaction of glycosylglycerides with water and other polar solvents we have surprisingly found that specific glycolipid materials from cereals have a behaviour which makes said lipid materials suitable and simple to utilise as a carrier material especially for pharmaceutical compositions, and also for other formulations, such as cosmetical, agricultural, nutritional and food applications.

SE 9400368-8 discloses an industrially applicable process for preparing a glycolipid material from plants, preferably cereals, by means of extraction and chromatographic separations. The glycolipid material so prepared can be used as an amphiphilic material in pharmaceutical products, cosmetics and food.

DESCRIPTION OF THE INVENTION

This invention relates to an oil-in-water emulsion comprising 0.01–50% by weight of the total preparation, preferably 0.1–10%, of an emulsifier and 0.1–70% by weight of the total preparation of an oily material emulsified in an polar solvent, characterised in that the emulsifier is a galactolipid material consisting of at least 50% digalactosyldiacylglycerols, the remainder being other polar lipids.

In a preferred preparation the galactolipid material consists of about 70–80% digalactosyldiacylglycerols and 20–30% other polar lipids.

In another preferred preparation the galactolipid material consists of up to 100% digalactosyldiacylglycerols.

The digalactosyldiacylglycerols can be described by the general formula

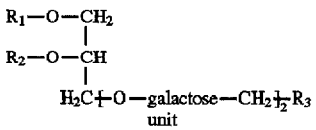

wherein $R_1$ and $R_2$ independently of each other are saturated or unsaturated fatty acid residues of 10–22 carbon atoms and 0–4 double bonds, or hydrogen; and $R_3$ is a hydroxyl or sulphonate group.

As preferred examples of fatty acid residues $R_1$ and $R_2$ can be mentioned naturally occurring fatty acyl groups, such as residues from the saturated acids palmitic ($C_{15}H_{31}CO$; 16:0) and stearic acid ($C_{17}H_{35}CO$; 18:0); from the monounsaturated acid oleic acid ($C_{17}H_{33}CO$; 18:1); and from the polyunsaturated acids linoleic ($C_{17}H_{31}CO$; 18:2) and linolenic acid ($C_{17}H_{29}CO$; 1813). The fatty acid residues can also contain hydroxy acids linked to the glycerol moiety with their hydroxyl groups esterified by further fatty acids, so called estolides.

The other polar lipids being part of the galactolipid material are a mixture of different glyco- and phospholipids, such as MGDG and phosphatidylcholines. The composition depends on the starting material and process used for the manufacture of the galactolipids.

The specific proportions of the components of the galactolipid material are not critical to the present invention as long as the content of DGDG is at least 50%. For many applications, however, the maximum benefits are realised by a high content of DGDG, the most important bilayer-forming component.

The galactolipid material can be extracted from almost any kind of plant material. Preferred plant materials are seeds and kernels from grains and cereals, for instance wheat, rye, oats, corn, rice, millet and sesame. Oat groats as well as wheat gluten have a high lipid concentration and are therefore of an advantage to use in the process of preparation. The digalactosyldiacylglycerols of the galactolipid material can, if applicable, also be of synthetic origin.

The oily material is any lipophilic material having a liquid or semi-solid consistency at room temperature. No particular limitation is imposed on the oily material. Plant oils, animal oils, synthetic oils, fatty acids, natural synthetic glycerides, and lipophilic drugs, etc., may be mentioned by way of example.

Preferred oils are plant oils containing γ-linolenic acid (GLA), such as evening primrose oils and borago oil, and fish oils containing eicosapentaenoic acid (EPA) and docosahexanoic acid (DHA).

The ratio between emulsifier and oily material could preferably be within the range of 1:40–1:10 by weight, especially 1:25–1:15 by weight.

An intrinsic beneficial feature of the galactolipids is the galactose units comprising the polar headgroup in each lipid molecule, which may sterically stabilise the emulsion droplets, and thus provide for a prolonged life-span when injected into the bloodstream.

Synthetic diglycosyldiacylglycerols based on galactose or any other monosaccharide unit, such as glucose, and natural glycosylglycerides, isolated from any source, based on other carbohydrate units than galactose, such as glucose, can be used in accordance with the invention.

The oil-in-water emulsions of the invention are prepared by using the galactolipid material as the emulsifier but may contain other low-molecular compounds in an effective isotonic amount. The oil-in-water emulsion may also comprise optional additives known in the art for improving different aspects of the composition, such as flavouring agents, colorants, thickening agents, co-surfactants, preservatives, antioxidants, etc.

The emulsions are prepared by conventional methods. For example, a 30% (w/w) emulsion of medium-chain triacylglycerol oil in water is prepared by dispersing the emulsifier, that is the galactolipid material, in the oil. Glycerol and water are mixed. The oil phase as well as the aqueous phase are preheated and then the oil phase is added to the aqueous phase under high shear mixing. It is then subjected to high-pressure homogenisation.

The invention also refers to a pharmaceutical composition comprising a therapeutically active substance in combination with the oil-in-water emulsion.

The therapeutically active substance can be a lipophilic drug such as anti-cancer agents, anti-microbial and particularly anti-fungal agents, immunosuppressant drugs like cyclosporin, dermatological drugs, psychotropic drugs, anaestethic drugs and other drugs which are lipophilic and which may present formulation problems which could be solved by the use of galactolipids.

A preferred oily material for the emulsion is in addition to the previous mentioned preferred oils also an MCT oil. There are also many lipids such as free fatty acids, mono-, di- and triacylglycerols, phospholipids, cholesterol esters and lipids of many other types which have therapeutic actions in themselves and which may be advantageously formulated in the form of an emulsion, based on the galactolipids. In this case the therapeutically active substance is the oily material, which can also have other bioactive properties.

A pharmaceutical composition can be as follows:
a therapeutically active substance in a therapeutically effective amount;
a galactolipid emulsifier, 0.1–5.0% by weight of the total composition;
an oily material, 1–50% by weight of the total composition;
optionally, an isotonic agent in an isotonically effective amount.

The isotonic agent is, for example, glycerol but could also be any isotonic agent in an isotonically effective amount.

The polar solvent can be water or aqueous solutions, such as buffers and saline, or any other conventional solvent, such as ethanol, glycerol, propylene glycol, polyethylene glycol, polypropylene glycol, glycofuran, methyl pyrrolidone, transcutol. Water is however the preferred solvent.

A pharmaceutical composition for parenteral administration can be as follows:
0.2–3% 2,6-diisopropylphenol,
0.3–5% galactolipid material,
5–30% triacylglycerol oil,
an isotonically effective amount of an isotonic agent,
ad 100% water.

The pharmaceutical composition may be formulated for oral, enteral, parenteral, rectal, vaginal, topical, ocular, nasal or aural administration to animals, especially mammals, including humans.

The emulsions based on the galactolipids are surprisingly stable preparations compared to phospholipid emulsions made from egg lecithin or soy lecithin. Shaking tests, which destroy phospholipid emulsions, have no effect on galactolipid emulsions.

The galactolipid emulsions also exhibit a narrow and consistent particle size distribution, which normally is a problem with the phospholipid emulsions. Commercially available fat emulsions based on egg lecithin often have a problem of containing particles that are too large, which may result in problems such as the creaming phenomenon or the appearance of oil droplets on the surface.

The galactolipid emulsions are also surprisingly stable to sterilisation by autoclaving in a standard autoclave. Commercially available fat emulsions often need to be autoclaved in special rotating autoclaves, which poses a technical problem. The use of standard autoclaving procedures is a pronounced industrial improvement provided by the invention.

Galactolipid Material

Galactolipid materials have been prepared from different cereals as stated below, and used for making carrier preparations and pharmaceutical compositions of the invention as stated in the examples. In the specification % refers to % by weight if not otherwise stated. The proportion of the solvents in solvent mixtures is given in parts by volume.

Galactolipid Material from Oats 200 kg of oat kernels (Kungsörnen AB, Sweden) were ground and extracted with 1000 l of 95% ethanol at 70° C.

for 3 h in an extraction tank under stirring. The slurry was centrifuged while still warm and separated from solid particles. The liquid fraction was evaporated at 60° C. which gave about 10 kg of a light brown oil.

The oil was applied to a stainless steel column containing 6.25 kg of silica gel (Martex Silica Si, particle size 20–45 pore diameter 60 Å, from Amicon Corp., USA). The column temperature was 50° C. The column was then washed with 30 l of a mixture of hexane:isopropanol, 90:10, in order to remove all nonpolar lipids.

The galactolipid material was then eluted from the column with 20 l of a mixture hexane:isopropanol, 60:40, giving a galactosyldiacylglycerol fraction. Evaporation of this fraction gave about 700 g of DGDG, the major lipid class. The galactolipid material was then dispersed in water and subjected to freeze-drying, which resulted in a free-flowing powder.

Enrichment of DGDG from Galactolipids 50 g galactolipids from oats, as obtained above, having a content of DGDG of about 70%, were dissolved in 250 ml hexane: isopropanol, 70:30, giving a total amount of 300 ml. The solution obtained was loaded on a silica gel (110 g) column and the less polar constituents were eluted with 1 l of the mixture of hexane:isopropanol, 70:30. The enriched DGDG fraction was eluted with 2 l acetone. The acetone was evaporated and freeze-dried. The total yield was 17 g of an almost pure DGDG product.

Hydrogenation of Galactolipids 200 g of a galactolipid mixture obtained from oats as stated above was dissolved in 2 l warm isopropanol. 15 g of a palladium on carbon catalyst (Pd 15%, moisture 53%, Engelhard Rome s.r.i., Italy) was placed in the bottom of a pressure reactor (Model No. 4552M; Parr Instrument Co., USA) equipped with two impellers on a stirrer shaft. The solution was then transferred into the reactor under a seal of nitrogen to reduce the fire hazard. The reactor vessel was sealed and first pressurized three times with nitrogen in order to remove air and then three times with hydrogen gas (Plus 4.5, from AGA Gas AB, Sweden). The hydrogen pressure was then kept at 6 bars, the stirrer set at 600 rpm and the mixture was heated to 70° C. It took 14 minutes for the reaction mixture to reach its temperature setpoint. The hydrogenation process was conducted for 6 hours after which the reaction product was filtered through a 0.45 μm filter in order to remove carbon particles and palladium. Solvent was evaporated on a rotavapor, the residual solid material was dispersed in 1600 ml of deionized water and freeze-dried.

The yield of hydrogenated galactolipids after filtration and freeze-drying was 155 g. The hydrogenation performance was evaluated by gas chromatography; only saturated fatty acids could be detected in the hydrogenated product.

Galactolipids from Wheat Gluten 1 kg of wheat gluten powder (AB Skånebrännerier, Sweden) was extracted with 4 l of 95% ethanol at 70° C. for 3 h in a beaker. The slurry was then filtered under a pressure of 400–500 kPa and the filtercake obtained was washed with 1 l of warm 95% ethanol. The combined ethanol solutions were evaporated at maximum 60° C. and gave about 60 g of a yellow oil.

The oil was applied to a stainless steel column containing 45 g of silica gel (Martex Silica Si, particle size 20–45 μm, pore size 60 Å, from Amicon Corp., USA). The column was then washed with 700 ml of a mixture hexane:isopropanol, 90:10, in order to remove neutral lipids.

In order to remove MGDG and some other polar lipids the column was subsequently washed with 1000 ml of a mixture hexane: isopropanol, 70:30. Elution of DGDG was carried out with 1000 ml of pure acetone. After evaporation about 4 g of an almost pure DGDG product was obtained.

Galactolipids from Rye 100 g rye flakes (Kungsörnen AB, Sweden) were stirred for 60 min in a mixture of industral hexane and isopropanol, 90:10. The slurry was filtered and evaporated which gave 0.5 g polar lipids. The residue, dissolved in 10 ml of a mixture of hexane and iso-propanol, 70:30, was loaded on three Sep-pak Silica plus columns (Millipore Corp., USA) connected in series, washed with 20 ml of the same mixture of solvents and eluted with 15 ml acetone. The eluate was evaporated and freeze-dried and the yield was 47 mg of galactolipids.

Chemical and Physical Characterization of Different Galactolipid Materials

Lipid Class Analysis

Lipid class analysis was performed by high performance liquid chromatography, HPLC, using a column packed with diol-modified silica (LiChrosphere 100 DIOL, 5 μm, 250 mm×4 mm i.d.; E. Merck, Germany). The column was enclosed in a water bath held at 75° C. The analytical system consisted of a HPLC pump CM 4000 (LDC/Milton Roy, USA), and an injector, model 7125, with a 20 l injection loop (Rheodyne Inc., USA). The evaporative light-scattering detector used was a Sedex 45 (S.E.D.E.R.E., France) equipped with a Sedex 55 nebulisation chamber with a drift tube temperature and air inlet pressure of 97° C. and 2.0 bar, respectively.

The flow of the mobile phase was 1 ml/min during the analysis. A binary solvent gradient, linear over 25 min, was used starting with 100% of A and ending with 100% of B, where A=hexane:isopropanol:n-butanol:tetrahydrofuran:isooctane:water, 64:20:6:4.5:4.5:1, and B=isopropanol:n-butanol:tetrahydrofuran:isooctane:water, 75:6:4.5:4.5:10. All solvents contained ammonium acetate, 180 mg/l.

Data collection and processing were done with GynkoSoft Data system version 4.22 (Softron GmbH, Germany). Typical amount injected for analysis was 100 μg. Identification was based on retention time comparison with authentic standards (Karlshamns LipidTeknik AB, Sweden). Volatile compounds were not detected in this system. Quantification was based on peak area calculations.

Zeta potentials were determined on dilute aqueous galactolipid dispersions with a Zetasizer 4 instrument (Malvern Instruments Ltd., UK)

TABLE 1

| Characterisation of different galactolipid materials | | | | | | |
|---|---|---|---|---|---|---|
|  | o-GL | o-h-GL | o-DGDG | w-GL | w-DGDG | r-GL |
| DGDG content, area % | 73 | 70 | 72 | 100 | 80 | 100 | 67 |
| Z-potential, mV | −74 | −76 | −30 | −51 | −75 | −38 | −37 |

In this Table 1 as well as in Table 2 below the following abbreviations are used o-GL=galactolipids from oats o-h-GL=hydrogenated galactolipids from oats o-DGDG=enriched galactolipids from oats w-GL=galactolipids from wheat w-DGDG=enriched galactolipids from wheat r-GL=galactolipids from rye

Fatty Acid Analysis

Analysis of the fatty acid profile was done by gas chromatography after transesterification of the lipids to fatty acid methyl esters. These were separated and quantified by capillary column gas chromatography on a Varian 3500 Capillary Gas Chromatograph equipped with a capillary column 30 m×0.25 mm i.d. (DB-WAX; J&W Scientific, USA), an on-column injector and a flame ionization detector. Helium was used as the carrier gas. Integration was performed with GynkoSoft Data system version 4.22 (Softton GmbH, Germany). Transesterification was done by adding 1 mg of a lipid sample to 2 ml of dimethyl carbonate:isooctane, 1:1. 1 ml of a solution containing 2.3 g sodium dissolved in 200 ml of methanol was added and the test tube was shaken vigorously for 30 s and left at room temperature for 15 min to ensure complete reaction. 3 ml water was added and the test-tube was shaken and then centrifuged at 2×g. 0.5 µl of the organic layer was injected on the chromatograph with the following separation conditions. The oven was temperature programmed, starting at 130° C. (2 min), increased to 150° C. (30°/min) and 220° C. (3.2° C./min) with a 10 min hold. The injector temperature was 130° C. and the detector temperature was 250° C. Initially the gas flow was 2.7 ml/min. The results are expressed as normalized weight percentages using the external standard method. No correction factors are used for the minor constituents for which standards are not available or acceptably pure.

TABLE 2

Characterisation of fatty acid composition

| Fatty acid composition, weight % | o-GL | o-h-GL | o-DGDG | w-GL | w-DGDG | r-GL |
|---|---|---|---|---|---|---|
| C 14:0 | | | | | | |
| C 16:0 | 20 | 21 | 21 | 16 | 15 | 13 | 12 |
| C 18:0 | 1 | 1 | 74 | 2 | 1 | 1 | |
| C 18:1 n-9 | 17 | 17 | | 19 | 6 | 5 | 8 |
| C 18:1 n-7 | 1 | 1 | | 1 | 1 | 1 | 1 |
| C 18:2 n-6 | 53 | 52 | | 58 | 71 | 68 | 69 |
| C 18:3 n-3 | 2 | 2 | | 3 | 3 | 3 | 5 |
| Minors <1% and unidentified | 6 | 6 | 5 | 1 | 3 | 8 | 5 |

NMR Spectroscopy of Digalactosyldiacylglycerols

One-dimensional proton-decoupled natural abundance $^{13}$C NMR spectra were recorded on a Bruker AM-400 spectrometer (Bruker Analytische Messtechnik GmbH., Germany) at a $^{13}$C frequency of 100.614 MHz. The pulse angle was 36°, the pulse repetition time 1.0 s and resolution 1.526 Hz per data point. 3 Hz line broadening was applied during processing. The samples (10–40 mg) were diluted in a mixture of 730 µl DMSO-d$_6$ (Aldrich Chemical Comp., Inc., USA) and 20 µl D$_2$O (Aldrich Chemical Comp., Inc., USA) and transferred to an NMR tube (5 mm i.d.).

TABLE 3

$^{13}$C Chemical shifts (ppm) of digalactosyldiacylglycerols from wheat and oats

| Signal | w-DGDG | o-DGDG |
|---|---|---|
| Fatty acid moieties | | |
| C(n) | 13.8 | 13.7 |
| C(n-1) | 21.9 | 21.9 |
| C(n-2) | 30.8 | 30.8 |
| C, methylene | 28.3–28.9 | 28.4–29.0 |
| C, allylic | 26.5 | 26.5 |
| C, doubly allylic | 25.1 | 25.1 |
| C, olefinic | 127.6–129.6 | 127.6–129.5 |
| C3 | 24.3 | 24.3 |
| C2 | 33.3, 33.5 | 33.3, 33.5 |
| C1 | 172.2, 172.5 | 172.1, 172.4 |
| Glycerol moiety | | |
| sn-1 | 62.3 | 62.4 |
| sn-2 | 69.8 | 69.8 |
| sn-3 | 66.6 | 66.6 |
| Digalactosyl moiety | | |
| C1 (inner) | 103.6 | 103.6 |
| C1' (outer) | 99.4 | 99.4 |
| others | 60.4, 66.3, 67.7, 68.2, 68.6, 69.3, 70.1, 71.1, 72.8, 72.8 | 60.4, 66.3, 67.7, 68.2, 68.6, 69.3, 70.1, 71.1, 72.8, 72.9 |

EXAMPLES

In the examples below commercially available chemicals were used without further purification if not otherwise stated. Deionised, membrane-filtered water was used in all preparations. Soybean oil and medium-chain triacylglycerol (MCT) oil, fish oils and oils with high contents of γ-linolenic acid (GLA), obtained from evening primrose seeds, were used as model oils. However, the type of oily matter is not crucial to obtain the specific benefits of the present invention.

Soybean oil, corn oil, and MCT oil were manufactured by Karlshamns AB, Sweden, and chromatographically purified. Evening primrose oils with different contents of GLA, free GLA, and fish oils were manufactured by Callanish Ltd., Scotland, and used as received, except the fish oils which were chromatographically purified.

The antioxidants ascorbyl palmitate and E 442 (ammonium phosphatides) were obtained from Roche Products Ltd., UK, and Palsgaard AS, Denmark, respectively.

The emulsions were prepared by high-pressure homogenisation, using different equipment as stated in the examples. The particle (droplet) size distributions and the zeta potential of the resulting emulsions were determined by dynamic light scattering (Zetasizer 4; Malvern Instruments Ltd., UK) at room temperature. The particle size measurements were carried out at an angle of 90°, using a AZ104 cell and multimodal analysis. Data are reported as Z averages. Zeta potentials were measured with the same cell with the following instrumental settings: Cross beam mode, F(ka)= 1.50 and cell voltage 134 V.

Example 1

Preparation of a 10% Fat Emulsion (MCT Oil)

An oil-in-water emulsion (batch size 200 g) was prepared containing the following ingredients:

| Ingredient | % |
| --- | --- |
| Emulsifier | 0.5 |
| MCT oil | 10.0 |
| Glycerol, 99% | 2.3 |
| Water | ad 100.0 |

The emulsifier, that is the galactolipid, was dispersed in the oil. Glycerol and water were mixed. The oil phase and the aqueous phase were preheated to 70° C. and 85° C., respectively. The aqueous phase was added to the oil phase under high shear mixing at 18,000 rpm for 6 min. The preemulsion was then homogenised at 80 MPa and 50° C. for 6 cycles (Mini-Lab 8.30 H; APV Rannie AS, Denmark). The emulsion formed had an average droplet size of 243 nm.

Example 2

Preparation of a 20% Fat Emulsion (MCT Oil)

An oil-in-water emulsion (batch size 200 g) was prepared containing the following ingredients:

| Ingredient | % |
| --- | --- |
| Emulsifier | 1.0 |
| MCT oil | 20.1 |
| Glycerol, 99% | 2.3 |
| Water | ad 100.0 |

The emulsifier, that is the galactolipid, was dispersed in the oil. Glycerol and water were mixed. The oil phase was preheated to 90° C. and the aqueous phase to 50° C. The oil phase was added to the aqueous phase under high shear mixing at 14,000 rpm for 4 min. The preemulsion was then homogenised at 80 MPa and 45° C. for 5 cycles (Mini-Lab 8.30 H; APV Rannie AS, Denmark). The emulsion formed had an average droplet size of 213 nm. This average size was not significantly altered by autoclaving (121° C., 20 min) and shaking (120 h, 150 cycles/min).

Example 3

Preparation of a 30% Fat Emulsion (MCT Oil)

An oil-in-water emulsion (batch size 200 g) was prepared using the following ingredients:

| Ingredient | % |
| --- | --- |
| Emulsifier | 1.5 |
| MCT oil | 30.1 |
| Glycerol, 99% | 2.3 |
| Water | ad 100.0 |

The emulsifier, that is the galactolipid, was dispersed in the oil. Glycerol and water were mixed. The oil phase was preheated to 67° C. and the aqueous phase to 55° C. The oil phase was added to the aqueous phase during high shear mixing at 13,000 rpm for 6 min. The preemulsion was then homogenised at 80 MPa and 40° C. for six cycles (Mini-Lab 8.30 H; APV Ranhie AS, Denmark), which resulted in an average droplet size of 200 nm.

One part of the resulting emulsion was heat sterilized in a standard bench autoclave at 121° C. for 20 min. After the heat treatment a droplet size of 209 nm was determined, indicating that the emulsion droplets were not significantly affected during the process.

Another part of the emulsion was exposed to a shaking test at 150 cycles/min for 5 days. No aggregation of the emulsion droplets and subsequent creaming could be observed after the shaking test. The average droplet size, 206 nm, indicated that the emulsion was very stable against shaking at high frequency for a long period of time. Also the heat sterilized emulsion was exposed to the same shaking test without any noticeable change in test performance.

An emulsion based on 1.2% egg phospholipids and 20% soybean oil did not withstand the shaking test at the same frequency; creaming could be observed on the top of the egg phospholipid emulsion after 1–2 hours.

Example 4

Preparation of a 39% Fat Emulsion (MCT Oil)

An oil-in-water emulsion (batch size 200 g) was prepared using the following ingredients:

| Ingredient | % |
| --- | --- |
| Emulsifier | 2.0 |
| MCT oil | 39.4 |
| Water | ad 100.0 |

The emulsifier, that is the galactolipid, was dispersed in the oil. Water and the oil phase were preheated to 70° C. and the oil was added to the aqueous phase under high shear mixing at 16,000 rpm for 7 min. The preemulsion was then homogenised at 82 MPa and 50° C. for 6 cycles (Mini-Lab 8.30 H; APV Ranhie AS, Denmark). This formulation gave an emulsion with a slightly creamy consistency and a narrow size distribution with an average droplet size of 206 nm.

Example 5

Preparation of a 50% Fat Emulsion (MCT Oil)

An oil-in-water emulsion (batch size 200 g) was prepared containing the following ingredients:

| Ingredient | % |
| --- | --- |
| Emulsifier | 2.5 |
| MCT oil | 50.3 |
| Glycerol, 99% | 2.3 |
| Water | ad 100.0 |

The emulsifier, that is the galactolipid, was dispersed in the oil. Glycerol and water were mixed. The oil phase was preheated to 60° C. and the aqueous phase to 75° C. The oil phase was added to the aqueous phase under high shear mixing at 20,000 rpm for 4.5 min. The preemulsion was then homogenised at 80 MPa and 55° C. for 5 cycles (Mini-Lab 8.30 H; APr Rannie AS, Denmark). The emulsion formed was quite high in viscosity ("yoghurt-like") with an average droplet size of 235 nm.

Example 6

Preparation of a 20% Fat Emulsion (MCT/Soybean Oil)

An oil-in-water emulsion (batch size 200 g) was prepared containing the following ingredients:

| Ingredient | % |
| --- | --- |
| Galactolipid material | 1.0 |
| Phosphatidylcholine from soybean | 1.0 |
| Soybean oil | 10.0 |
| MCT oil | 10.0 |
| Glycerol, 99% | 2.3 |
| Water | ad 100.0 |

The galactolipid material and soybean phosphatidylcholine were dispersed in the oil mixture. Glycerol and water were mixed. The oil phase was preheated to 65° C. and the aqueous phase to 55° C. The aqueous phase was added to the oil phase under high shear mixing at 11,000 rpm for 9 min. The preemulsion was then homogenised at 80 MPa and 46° C. for 5 cycles (Mini-Lab 8.30 H; APV Rannie AS, Denmark). The emulsion formed had an average droplet size of 262 nm which did not change significantly after autoclaving.

Example 7

Preparation of a 20% Fat Emulsion (Soybean Oil)

An oil-in-water emulsion (batch size 200 g) was prepared using the following ingredients:

| Ingredient | % |
| --- | --- |
| Emulsifier | 1.5 |
| MCT oil | 20.0 |
| Glycerol, 99% | 2.3 |
| Water | ad 100.0 |

The emulsifier, that is the galactolipid, was dispersed and hydrated in a portion of the water. Glycerol and the rest of the water was then added and mixed. The aqueous dispersion was subjected to high pressure homogenisation for 2 cycles at 60 MPa and 40° C. The soybean oil, preheated to 40° C., was added to the aqueous dispersion under high shear mixing at 13,000 rpm for 10 min. The preemulsion was then homogenised at 80 MPa and 40° C. for 6 cycles (Mini-Lab 8.30 H; APV Rannie AS, Denmark). After cooling to room temperature, the emulsion was adjusted to pH 7.2 using a 2M NaOH solution.

Table 4 summarizes the average droplet size in nm of the emulsions described in Examples 1–7.

In addition zeta potential values in mV are listed in Table 4 indicating that the emulsion droplets carried a significant negative charge which implies a good shelf life of the emulsions.

TABLE 4

| Ex. no. | Oily material | Initial emulsion | After autoclaving | After shake test | Zeta potential |
| --- | --- | --- | --- | --- | --- |
| 1 | 10% MCT oil | 243 | | | −69 |
| 2 | 20% MCT oil | 213 | 226 | 222 | −72 |
| 3 | 30% MCT oil | 200 | 209 | 206 | −68 |
| 4 | 39% MCT oil | 206 | 216 | | −71 |
| 5 | 50% MCT oil | 235 | | | −72 |
| 6 | 10% MCT oil 10% soybean oil | 262 | 266 | | −69 |
| 7 | 20% soybean oil | 400 | | | −77 |

Example 8

Preparation of a 20% Fat Emulsion (Evening Primrose Oil Containing 9% GLA)

An oil-in-water emulsion (batch size 200 g) was prepared with the following ingredients:

| Ingredient | % |
| --- | --- |
| Emulsifier, hydrogenated | 1.02 |
| Evening primrose oil | 20.46 |
| Water | ad 100.00 |

The emulsifier, that is the hydrogenated galactolipid, was dispersed in the oil. The oil phase and water were preheated to 62° C. and 73 ° C., respectively, and the oil phase was added to the water under high shear mixing at 14,000 rpm for 2.5 min. The preemulsion was then homogenised at 80 MPa and 56° C. for 7 cycles (Mini-Lab 8.30 H; APr Rannie AS, Denmark). This formulation gave an emulsion with an average droplet size of 240 nm. The zeta potential was −57 mV.

Example 9

Preparation of a 20% Fat Emulsion (Evening Primrose Oil Containing 9% GLA)

An oil-in-water emulsion (batch size 200 g) was prepared with following ingredients:

| Ingredient | % |
| --- | --- |
| Emulsifier, enriched | 1.01 |
| Evening primrose oil | 20.16 |
| Water | ad 100.00 |

The emulsifier, that is the enriched galactolipid, was dispersed in the oil. The oil phase and water were preheated to 64° C. and 63° C., respectively, and the oil phase was added to the water under high-shear mixing at 13,500 rpm for 2.5 min. The preemulsion was then homogenised at 80 MPa and 50° C. for 7 cycles (Mini-Lab 8.30 H; APV Ranhie AS, Denmark). This formulation gave an emulsion with an average droplet size of 260 nm and a zeta potential of −50 mV.

Example 10

Preparation of a 40% Fat Emulsion (Evening Primrose Oil Containing 9% GLA)

An oil-in-water emulsion (batch size 300 g) was prepared with the following ingredients:

| Ingredient | % |
| --- | --- |
| Emulsifier | 1.99 |
| Evening primrose oil | 39.55 |
| Vitamin E acetate | 1.08 |
| Ammonium phosphatides, E 442 | 0.10 |
| Ascorbyl palmitate | 0.02 |
| Sucrose | 14.08 |
| Lemon flavour | 2.00 |
| Potassium sorbate | 0.10 |
| Citric acid | 0.01 |
| Water | ad 100.0 |

The emulsifier and antioxidants were dispersed in the oil. Sucrose, preservative, flavour and water were mixed. The oil phase and the aqueous phase were preheated to 60° C. and 68° C., respectively, and the oil was added to the aqueous phase under high shear mixing at 17,000 rpm for 4 min. The preemulsion was then homogenised at 80 MPa and 60° C. for 5 cycles (Mini-Lab 8.30 H; APV Rannie AS, Denmark).

This formulation gave an emulsion with an average droplet size of 230 nm and a zeta potential of −72 mV. The pH was 5.8.

Example 11

Preparation of a 36% Fat Emulsion (Evening Primrose Oil Containing 9% GLA)

An oil-in-water emulsion (batch size 2300 g) was prepared with the following ingredients:

| Ingredient | % |
| --- | --- |
| Emulsifier | 1.80 |
| Evening primrose oil | 35.97 |
| Vitamin E acetate | 1.09 |
| Ammonium phosphatides, E 442 | 0.10 |
| Ascorbyl palmitate | 0.02 |
| Sucrose | 15.00 |
| Banana flavour | 2.00 |
| Potassium sorbate | 0.10 |
| Water | ad 100.0 |

The emulsifier and antioxidants were dispersed in the oil. Sucrose, preservative, flavour and water were mixed. The oil phase and the aqueous phase were preheated to 58° C. and 63° C., respectively, and the oil was added to the aqueous phase under high shear mixing at 16,000 rpm for 7.5 min. The preemulsion was then homogenised (Model LAB, Type 12.51 H; APV Rannie AS, Denmark) at a total pressure of 50 MPa and a pressure of 10 MPa over the second stage. The flow was 0.82 l/min, the total time 12 min and the temperature 48° C. This formulation gave an emulsion with an average droplet size of 230 nm and a zeta potential of −72 mV.

Example 12

Preparation of a 40% Fat Emulsion (Enriched Evening Primrose Oil Containing 20% GLA)

An oil-in-water emulsion (batch size 300 g) was prepared with the following ingredients:

| Ingredient | % |
| --- | --- |
| Emulsifier | 2.49 |
| Enriched evening primrose oil, 20% GLA | 39.85 |
| Vitamin E acetate | 0.39 |
| Ammonium phosphatides, E 442 | 0.10 |
| Ascorbyl palmitate | 0.02 |
| Sucrose | 15.04 |
| Lemon flavour | 2.00 |
| Potassium sorbate | 0.10 |
| Water | ad 100.0 |

The emulsifier and antioxidants were dispersed in the oil. Sucrose, preservative, flavour and water were mixed. Both phases were preheated to 65°–70° C. and the oil was added to the aqueous phase under high shear mixing at 15,000 rpm for 3.5 min. The preemulsion was then homogenised at 80 MPa and 60° C. for 5 cycles (Mini-Lab 8.30 H; APr Rannie AS, Denmark). This formulation gave an emulsion with a thick yoghurt-like consistency.

Example 13

Preparation of an 11% Fat Emulsion (Enriched Evening Primrose Oil Containing 80% GLA)

100 g of an oil-in-Water emulsion was prepared-containing the following ingredients:

| Ingredient | % |
| --- | --- |
| Emulsifier, enriched | 1.0 |
| Enriched evening primrose oil, 80% GLA | 11.0 |
| Glycerol, 2.3% in water | ad 100.0 |

The emulsifier, that is the enriched galactolipid material, was dissolved in the oil at approximately 50° C. under nitrogen. Glycerol and water were mixed. The aqueous phase was added to the oil phase under high shear mixing at 12,000 rpm for 30 s. The preemulsion was heated to 35° C. and homogenised at 83 MPa for 5 min (EmulsiFlex-C30, Avestin Inc., Canada). The resulting emulsion had an average droplet size of 224 nm, a zeta potential of −40 mV, and was easily filtered through a membrane filter with a pore size of 0.22 μm.

Example 14

Preparation of a 20% Fat Emulsion (Free Fatty Acid Containing 70% GLA)

50 g of an oil-in-water emulsion was prepared containing the following ingredients:

| Ingredient | % |
| --- | --- |
| Emulsifier, enriched | 2.5 |
| Free fatty acid, 70% GLA | 20.0 |
| Glycerol, 2.3% in water | ad 100.0 |

The emulsifier, that is the enriched galactolipid material, was dissolved in the free fatty acid at approximately 50° C. under nitrogen. Glycerol and water were mixed. The aqueous phase was added to the oil phase under high shear mixing at 12,000 rpm for 30 s. The preemulsion was heated to 35° C. and homogenised at 86 MPa for 6.5 min (EmulsiFlex-C30, Avestin Inc., Canada). The resulting emulsion had an average droplet size of 211 nm, a zeta potential of −40 mV, and was easily filtered through a membrane filter with a pore size of 0.22 μm.

Example 15

Preparation of a 39% Fat Emulsion (Sardine Oil in Eicosapentaenoic Acid (EPA))

An oil-in-water emulsion (batch size 250 g) was prepared with the following ingredients:

| Ingredient | % |
| --- | --- |
| Emulsifier | 3.88 |
| Sardine oil | 38.93 |
| Vitamin E acetate | 1.08 |
| Ammonium phosphatides, E 442 | 1.00 |
| Ascorbyl palmitate | 0.02 |
| Sucrose | 14.98 |
| Peppermint flavour | 1.00 |
| Potassium sorbate | 0.20 |
| Water | ad 100.0 |

The emulsifier and antioxidants were dispersed in the oil. Sucrose, preservative, flavour and water were mixed. The oil phase and the aqueous phase were preheated to 57° C. and 51° C. respectively and the oil was added to the aqueous phase under high shear mixing at 16,000 rpm for 3.5 min.

The preemulsion was then homogenised at 80 MPa and 55° C. for 7 cycles (Mini-Lab 8.30 H; APV Rannie AS, Denmark). This formulation gave an emulsion with an average droplet size of 190 nm and a zeta potential of −72 mV.

Example 16

Preparation of a 39% Fat Emulsion (Tuna Fish Oil Rich in Docosahexanoic Acid (DHA)

An oil-in-water emulsion (batch size 250 g) was prepared with the following ingredients:

| Ingredient | % |
|---|---|
| Emulsifier | 3.91 |
| Tuna fish oil | 39.08 |
| Vitamin E acetate | 1.10 |
| Ammonium phosphatides, E 442 | 1.00 |
| Ascorbyl palmitate | 0.02 |
| Sucrose | 14.94 |
| Peppermint flavour | 1.00 |
| Potassium sorbate | 0.20 |
| Water | ad 100.0 |

The emulsifier and antioxidants were dispersed in the oil. Sucrose, preservative, flavour and water were mixed. The oil phase and the aqueous phase were preheated to 59° C. and 64° C. respectively and the oil was added to the aqueous phase under high shear mixing at 16,000 rpm for 5 min. The preemulsion was then homogenised at 80 MPa and 60° C. for 7 cycles (Mini-Lab 8.30 H; APV Rannie AS, Denmark). This formulation gave an emulsion with an average droplet size of 190 nm and a zeta potential of −75 mV.

Example 17

Preparation of a 40% Fat Emulsion (Corn Oil)

An oil-in-water emulsion (batch size 200 g) was prepared with the following ingredients:

| Ingredient | % |
|---|---|
| Emulsifier | 2.00 |
| Corn oil | 40.08 |
| Ammonium phosphatides, E 442 | 1.00 |
| Ascorbyl palmitate | 0.02 |
| Sucrose | 14.98 |
| Potassium sorbate | 0.10 |
| Water | ad 100.0 |

The emulsifier and antioxidants were dispersed in the oil. Sucrose, preservative, and water were mixed. Both phases were preheated to 65° C. and the oil was added to the aqueous phase under high shear mixing at 15,000 rpm for 4 min. The preemulsion was then homogenised at 80 MPa and 55° C. for 7 cycles (Mini-Lab 8.30 H; APV Rannie AS, Denmark). This formulation gave an emulsion with a narrow size distribution and an average droplet size of 210 nm and a zeta potential of −74 mV.

Example 18

Preparation of a 11% Parenteral Fat Emulsion (Soybean Oil) Containing 2,6-Diisopropylphenol An oil-in-water emulsion (batch size 150 g) containing a pharmacologically active compound was prepared using the following ingredients:

| Ingredient | % |
|---|---|
| Emulsifier | 1.27 |
| Soybean oil | 10.57 |
| 2,6-diisopropylphenol | 1.05 |
| Glycerol, 99% | 2.24 |
| Water | ad 100.00 |

The emulsifier, that is the galactolipid, and the active ingredient, an anaesthetic drug, were dissolved in the soybean oil. Glycerol and water were mixed. The aqueous dispersion and the drug-containing oil phase were preheated to 72° C. and 68° C., respectively. The oil phase was added to the aqueous dispersion under high shear mixing at 13,000 rpm for 1.5 min. The preemulsion was then homogenised at 80 MPa and 48° C. for 7 cycles (Mini-Lab 8.30 H; APV Ranhie AS, Denmark). The emulsion formed had an average droplet size of 170 nm and a zeta potential of −63 mV. The osmolality determined with a microosmometer (Type 13; Hermann Roebling Messtechnik, Germany) was 257 milliosmol/kg $H_2O$.

Conclusions

Our findings related to the invention are that it is possible to produce remarkably stable oil-in-water emulsions based on the galactolipid material, which fulfils the important and necessary requirements of being autoclavable and resistant to harsh mechanical treatments. The emulsions have particle size distributions which are suitable for parenteral and intravenous use. The emulsions do not exhibit any unpleasant odour or taste and they are remarkably stable towards oxidation. This invention provides an alternative to the phospholipid emulsions which offers concrete advantages compared to such emulsions.

We claim:

1. An oil-in water emulsion comprising an emulsifier in an amount of about 0.01–50% by weight of the total preparation, an oily material emulsified in a polar solvent in an amount of about 0.1–70% by weight of the total preparation, and polar lipids in the remaining amount of the total preparation, wherein the emulsifier is a galactolipid material consisting of at least 50% digalactosyldiacylglycerols, and wherein the ratio of the emulsifier and the oily material is about 1:10 to about 1:40 by weight.

2. An emulsion according to claim 1, wherein the galactolipid material consists of about 70–80% digalactosyldiacylglycerols and about 20–30% other polar lipids.

3. An emulsion according to claim 1, wherein the galactolipid material consists up to 100% digalactosyldiacylglycerols.

4. An emulsion according to claim 1, wherein the oily material comprises γ-linolenic acid in the form of a free acid, its salts or esters.

5. An emulsion according to claim 1, wherein the oily material is an evening primrose oil or a borago oil.

6. A pharmaceutical, nutritional or cosmetic composition which comprises the emulsion of claim 1 as a carrier for an active substance.

7. A pharmaceutical composition comprising an oil-in-water emulsion according to claim 1 further comprises a therapeutically active substance.

8. A pharmaceutical composition according to claim 7, wherein the oily material comprises γ-linolenic acid in the form of a free acid, its salts or esters.

9. A pharmaceutical composition according to claim 7, wherein the oily material is an evening primrose oil or a borago oil.

10. A pharmaceutical composition according to claim 7, wherein the oily material is a triacylglycerol oil.

11. A pharmaceutical composition according to claim 7, comprising:
- a therapeutically active substance in a therapeutically effective amount;
- a galactolipid emulsifier in an amount of about 0.1–5.0% by weight of the total composition;
- an oily material in an amount of about 1–50% by weight of the total composition;
- optionally, an isotonic agent in an isotonically effective amount; and
- a polar solvent.

12. A pharmaceutical composition for parenteral administration according to claim 10, consisting of, by weight of the total composition,
- about 0.2–3% 2,6-diisopropylphenol,
- about 0.3–5% galactolipid material,
- about 5–30% triacylglycerol oil,
- about an isotonically effective amount of an isotonic agent, and
- about 100% water.

13. A pharmaceutical composition according to claim 7 for oral, enteral, parenteral, rectal, vaginal, topical, ocular, nasal or aural administration.

14. An oil-in-water emulsion according to claim 1 wherein the emulsifier is in an amount of about 0.1–10% by weight of the total preparation.

15. A pharmaceutical composition according to claim 7, wherein the oily material is a medium-chain triacylglycerol oil or a bioactive substance.

16. An oil-in-water emulsion according to claim 1 wherein the ratio of the emulsifier and the oily material is about 1:15 to about 1:25 by weight.

* * * * *

UNITED STATES PATENT AND TRADEMARK OFFICE
CERTIFICATE OF CORRECTION

PATENT NO. : 5,688,528
DATED : November 18, 1997
INVENTOR(S) : Carlsson et al.

It is certified that error appears in the above-identified patent and that said Letters Patent is hereby corrected as shown below:

Column 16,
Lines 43-53, now reads "An oil-in water emulsion comprising an emulsifier in an amount of about 0.01-50% by weight of the total preparation, an oily material emulsified in a polar solvent in the amount of about 0.1-70% by weight of the total preparation, and polar lipids in the remaining amount of the total preparation, wherein the emulsifier is a galactolipid material consisting of at least 50% digalactosyldiacylglycerols, and wherein the ratio of the emulsifier and the oily material is about 1:10 to about 1:40 by weight." and should read -- An oil-in water emulsion comprising an emulsifier in an amount of about 0.01-50% by weight of the total preparation, and an oily material emulsified in a polar solvent in an amount of about 0.1-70% by weight of the total preparation, wherein the emulsifier is a galactolipid material consisting of at least 50% digalactosyldiacylglycerols and a remainder of other polar lipids, and wherein the ratio of the emulsifier and the oily material is about 1:10 to about 1:40 by weight. --

Signed and Sealed this

Nineteenth Day of July, 2005

JON W. DUDAS
*Director of the United States Patent and Trademark Office*